United States Patent
Reginster et al.

(10) Patent No.: US 7,728,112 B2
(45) Date of Patent: *Jun. 1, 2010

(54) METHOD FOR MONITORING COLLAGEN TYPE II DEGRADATION IN CARTILAGE

(75) Inventors: Jean-Yves Reginster, Angleur (BE); Michelle Deberg, Embourg (BE); Yves Henrotin, Beaufays (BE); Stephan Christgau, Gantofte (DK)

(73) Assignee: Universite de Liege, Liege (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/222,352

(22) Filed: Aug. 7, 2008

(65) Prior Publication Data

US 2009/0042220 A1 Feb. 12, 2009

Related U.S. Application Data

(62) Division of application No. 10/507,498, filed as application No. PCT/EP03/02561 on Mar. 12, 2003, now Pat. No. 7,410,770.

(60) Provisional application No. 60/363,926, filed on Mar. 13, 2002.

(30) Foreign Application Priority Data

Mar. 13, 2002 (DK) ................................ 2002 00380

(51) Int. Cl.
*C07K 16/18* (2006.01)
*G01N 33/53* (2006.01)
*G01N 33/543* (2006.01)

(52) U.S. Cl. .................... 530/387.9; 435/7.1; 435/7.93; 436/518; 422/61

(58) Field of Classification Search ........................ None
See application file for complete search history.

(56) References Cited

U.S. PATENT DOCUMENTS

| | | | | |
|---|---|---|---|---|
| 5,641,837 | A | 6/1997 | Eyre | 435/7.1 |
| 5,919,634 | A | 7/1999 | Eyre | 435/7.1 |
| 6,132,976 | A | 10/2000 | Poole et al. | 435/7.1 |
| 6,342,361 | B1 | 1/2002 | Qvist et al. | 435/7.1 |
| 7,148,020 | B2 | 12/2006 | Holmdahl et al. | |

FOREIGN PATENT DOCUMENTS

WO     WO01/38872     5/2001

OTHER PUBLICATIONS

Deberg et al. "New serum biochemical markers (Coll 2-1 and Coll 2-1 NO2) for studying oxidative-related type II collagen network degradation in patients with osteoarthritis and rheumatoid arthritis" OsteoArthritis and Cartilage (2005) 13, 258-265.*
Cook et al., "Antibodies to type II collagen in early rheumatoid arthritis: Correlation with disease progression" Arthritis Rheum. Oct. 1996;39(10):1720-7.*
Abdullah et al. "Molecular requirements for hapten binding to antibodies against glutamate and aspartate" Neuroscience. Dec. 1992;51(3):729-38.*
Coffey et al. "Digestion of native collagen, denatured collagen, and collagen fragments by extracts of rat liver lysosomes" J Biol Chem. Sep. 10, 1976;251(17):5280-2.*
Harlow, E. and Lane, D., Antibodies: A Laboratory Manual (1988) Cold Spring Harbor Laboratory Press, Cold Spring Harbor, NY, pp. 141-142.*
Harlow et al., Antibodies: A Laboratory Manual (1988) Cold Spring Harbor Laboratory Press, Cold Spring Harbor, NY, pp. 72-76.
Kuby, Immunology, W.H. Freeman and Company (1992), p. 125.
Janeway et al., Immunobiology: the Immune System in Health and Disease (1999), Elsevier Science Ltd/Garland Publishing, New York, NY Fourth Edition, pp. 34-35.
Deberg et al., "One-year increase of Coll 2-1, a new marker of type II collagen degradation, in urine is highly predictive of radiological OA progression" *Osteoarthritis and Cartilage*, 13 (2005), pp. 1059-1065.
Billinghurst et al, J. Clin. Invest, vol. 99, No. 7, Apr. 1997, pp. 1534-1545, Enhanced Cleavage of Type II Collagen by . . . .
Croucher et al, J Clin Pathol Mol Pathol, 52, 1999, pp. 323-331 Differential detection of type II collagen N-terminal and . . . .
Dodge et al, J. Clin. Invest., vol. 83, Feb. 1989, pp. 647-661, Immunohistochemical Detection and Immunochemical Analysis of . . . .
Furumitsu et al, Jour of Rheumatology, 27, 2000, pp. 64-70, Levels of Serum and Synovial Fluid Pyridinium Crosslinks in . . . .
Henrotin et al, XP-002258974, Type II Collagen Derived Fragment (Coll 2-1) is New Marker Predictive of Osteoarthritis . . . p. S17, Osteopor. Int. vol. 13, No. 53 (Nov. 2002) Abstract No. 02.
Hollander et al, J. Clin. Invest., vol. 93, Apr. 1994, pp. 1722-1732, Increased Damage to Type II Collagen in . . . .
Wollheim, APMIS 104, pp. 81-93, 1996, Predictors of joint damage in rheumatoid arthritis.
Soinila et al, Jour of Histochem and Cytochem, vol. 40, No. 2, pp. 231-239, 1992, Immunohistochemistry of Enkephalins: . . . .
Moller, Scand J Clin Lab Invest, 58, 1998, pp. 269-278, Connective tissue markers of rheumatoid arthritis.

* cited by examiner

*Primary Examiner*—Mark L Shibuya
*Assistant Examiner*—Christine Foster
(74) *Attorney, Agent, or Firm*—Jacobson Holman PLLC (57) ABSTRACT

A method for improving the diagnostic assessment of cartilage degenerative processes, and to provide means of monitoring the effects of therapeutical measures taken towards arthritic diseases in most mammals utilizes an immunoassay to detect fragments of collagen type II resulting from collagenase activity comprising an antibody directed against an epitope comprised in the amino acid sequence HRGYPGLDG (SEQ ID NO:1), located in the helical region of collagen type II.

4 Claims, 5 Drawing Sheets

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial sequence
<220> FEATURE:
<223> OTHER INFORMATION: Synthesized
```

```
<400> SEQUENCE: 1

His Arg Gly Tyr Pro Gly Leu Asp Gly
1               5
```

METHOD FOR MONITORING COLLAGEN TYPE II DEGRADATION IN CARTILAGE

CROSS-REFERENCE OF RELATED APPLICATIONS

This is a divisional of application Ser. No. 10/507,498, filed, Sep. 13, 2004 now U.S. Pat. No. 7,410,770, which is a nationalization of PCT/EP03/02561, filed Mar. 12, 2003, and published in English, which claims the benefit of U.S. Provisional Application No. 60/363,926, filed Mar. 13, 2002.

The present invention relates to a method for evaluating cartilage catabolism by determining the level of collagen type II degradation products in a biological sample. In a preferred embodiment, the invention relates to an immunoassay comprising an antibody directed against a collagen type II specific epitope.

Cartilage matrix is synthesized, organized, maintained and degraded by a sparse population of chondrocytes. The properties of cartilage are critically dependent upon the structure and integrity of the extracellular matrix (ECM). In a normal cartilage the anabolic and catabolic processes of ECM formation and degradation are well balanced.

In joint diseases, such as rheumatoid arthritis (RA) and osteoarthritis (OA), the rate of degradation of the ECM often exceeds the rate of synthesis. Thereby the structural integrity and mechanical strength of the tissues is impaired, resulting in irreversible destruction of the joint structures.

Until now it has been difficult to assess directly the ongoing cartilage destruction in arthritis patients, because specific markers for this process have not been available in the clinical practice. Other markers used for assessment of RA patients, such as C-reactive protein and Rheumatoid factors are associated with the inflammatory process involved in the disease, but are not directly related to the level of cartilage destruction and they are not specific for RA. In OA these parameters have even less relevance for monitoring cartilage degradation.

The main structural component of cartilage is collagen type II, which is covalently cross-linked and assembled into fibres. Interspaced between the collagen network are long chains of the negatively charged polysaccharide hyaluronic acids, to which several large proteoglycans are attached. The collagen type II fibres are responsible for the tensile strength whereas the proteoglycans provide the compressive stiffness necessary for normal articulation and function. Mature collagen type II consist of a triple helical structure with short telopeptides in either end. The telopeptides cross-link covalently to other collagen molecules thereby packing individual collagen molecules into a rigid fibrillar network.

Degradation of collagen type II involves collagenases (MMP1, MMP8 and MMP13) (Billinghurst et al 1997). A characteristic collagenase cleavage site is found in the triple helical region of collagen type II between residues 775 and 776, which generates two fragments containing ¾ and ¼ of the intact collagen molecule. Antibodies, which recognize the C-terminal part of the COL2-¾fragment and the N-terminal part of the COL2-¼ fragments, have been developed (Hollander et al 1994). It has been demonstrated that the COL2-¾ epitope but not the COL2-¼ epitopes can be found in circulation, probably due to a higher resistance to proteolysis of the COL2-¾ fragment (Croucher and Hollander 1999). Specific immunoassays for detection of the COL2-¾ neoepitope in body fluids have been developed (U.S. Pat. No. 6,132,976). It has been reported that RA and OA patients assessed in a cross sectional study have elevated levels of this collagen type II derived marker, but further clinical data obtained with this marker has not been published.

The COL2-¾ and COL2-¼ fragments are approximately 75 kDa and 25 kDa respectively (Billinghurst et al 1997). Smaller collagen type II fragments, generated by additional proteolytic processing, may filter more readily into body fluids, especially renal filtration and subsidiary detection in urine require quite small fragments. Smaller fragments might yield a higher concentration and ease their detection. U.S. Pat. No. 6,132,976 describes detection of collagen type II fragments in synovial fluid and serum utilizing an epitope located within the COL2-¾ fragment, however it is not determined whether the fragment is the intact COL2-¾ fragment or proteinase cleaved fragments thereof.

Fragments generated from the telopeptidic region (U.S. Pat. No. 5,641,837, U.S. Pat. No. 5,919,634, U.S. Pat. No. 6,342,361) also filtrate more readily into body fluids, however these fragments are not generated as a result of collagenase activity, which is believed to be responsible for the initial collagen breakdown seen in joint diseases (Billinghurst et al 1997).

Detection of other cartilage derived metabolites, such as free urinary pyridinoline, cartilage oligomeric matrix protein (COMP), hyaluronates, aggrecan and collagen type III fragments, arising from destruction of joint tissues affected by an inflammatory disease have also been reported (Furumitsu et al 2000, Moller 1998, Wollheim 1996), and PCT application WO 01/38872). The clinical usefulness of these markers, however, remains to be proven.

Increased awareness of the early biochemical and structural changes in cartilage-related diseases in combination with the introduction of new disease suppressive agents has created the need to develop improved diagnostic methods to assess disease severity and prognosis. Thus the need for sensitive simple and reliable markers for cartilage degradation is evident, and such markers will fulfill important clinical purpose for management of arthritic diseases.

An object of the present invention is to improve the diagnostic methods for cartilage degenerative processes, and to provide means of monitoring the effects of therapeutical measures taken towards such diseases.

According to the present inventions a method for detecting and/or monitoring cartilage degradation is provided. The method enables such detection by measuring in a biological sample a collagen type II fragment wherein all or a relevant part of the amino acid sequence HRGYPGLDG (SEQ ID NO:1) is contained.

The method of the present invention will enable the monitoring of a catabolic process of a joint tissue as well as in growth plates and intervertebral disks, by detecting cartilage degradation. This will provide means for diagnosis, monitoring disease activity, disease progression and treatment efficacy.

Thus the present invention provides a method of qualitative or quantitative assay or collagen type II or fragments thereof in a biological sample comprising contacting said fragments with an immunological binding partner which is immunoreactive with an epitope comprised in the amino acid sequence HRGYPGLDG (SEQ ID NO:1) and detecting resulting immunoreaction.

The detection performed in the method of the present invention may be carried out with an immunoassay utilizing an antibody, which recognizes an epitope within the collagen type II derived sequence HRGYPGLDG (SEQ ID NO:1) or consisting of the whole of said sequence. To ensure monitoring of collagen type II degradation, a preferred embodiment provides an antibody, which only recognizes the unwound form of the epitope, and not the wound form.

The invention also includes a cell line for production of monoclonal antibodies recognizing an epitope comprised in the collagen type II derived sequence HRGYPGLDG (SEQ ID NO:1).

To employ the present invention a kit utilizing an antibody, which recognizes an epitope comprised in the collagen type II derived sequence HRGYPGLDG (SEQ ID NO:1), together with a suitable detection system, is provided. Supplements to such a kit are a second antibody and a synthetic peptide resembling the epitope. For detection such supplements can be labeled. The kit of the present invention can be applied to samples like mammalian body fluids, extracts from cells or tissues or supernatants from cells or tissues cultured in vitro.

The present invention relates to methods and techniques for the determination or quantification of cartilage catabolism, based on detection or quantification of characteristic collagen type II metabolites, especially in body fluids such as urine or serum.

As used herein, "immunological binding partner" includes polyclonal, monoclonal or humanized antibodies, including Fc fragments, Fab fragments, chimeric antibodies or other antigen-specific antibody fragments.

As used herein "collagen type II chain", means a single collagen type II polypeptide, encoded by the Col-II-A1gene.

As used herein "collagen type II/mature collagen type II", includes three collagen type II chains organized in one collagen type II molecule. In the collagen type II molecule, the chains are wound into a triple helical structure, and propeptides at either end are removed leaving short telopeptide sequences at the N- and C-terminal ends of the triple helix.

As used herein "collagen type II fibrils", means mature collagen type II, organized in a staggered array of fibres, where individual collagen type II molecules have been covalently cross-linked, involving characteristic lysine and histidine residues within the triple helical as well as telopeptide regions, and packed together side by side.

As used herein "collagen type II fibres", means an aggregation of fibrils into organized bundles within the cartilage extracellular matrix.

As used herein "collagen type II fragment", includes a polypeptide, domain structure, peptide or otherwise proteolytically processed protein fragment derived from a mature mammalian collagen type II molecule. The preferred collagen type II fragment is an unwound polypeptide or peptide.

As used herein "wound collagen type II", means mature collagen type II, where the three collagen type II chains are organized in the authentic triple helix structure.

As used herein "unwound collagen type II", means mature collagen type II, where the three collagen type II chains are no longer in the authentic triple helix structure, but disassembled or partly disassembled into single polypeptide chains.

In one embodiment of the present invention, collagen type II fragments containing all or a relevant part the following sequence HRGYPGLDG (SEQ ID NO:1) are detected in a biological sample to enable detection and monitoring of cartilage degradation. Detection of such collagen type II fragments can for example be performed using HPLC, mass spectroscopy, sequencing, or immunoassays. The HRGYPGLDG (SEQ ID NO:1) sequence is unique for the collagen type II chain and is located in the helical part of collagen type II (position 289-297 GeneBank accession nr. NP_001835 isoform 1 and position 220-228 GeneBank accession nr. NP_149162 isoform 2).

Fragments of collagen type II containing the epitope of the HRGYPGLDG (SEQ ID NO:1) sequence vary in size below 80 kDa. Smaller fragments, which can be excreted into urine, are detected in one embodiment of the present invention. These fragments may be smaller than 30 kDa or even more preferred smaller than 10 kDa.

One preferred method of detection is the use of an immunoassay, utilizing an antibody, which binds to an epitope on type II collagen or fragments thereof containing an epitope within the following sequence HRGYPGLDG (SEQ ID NO:1). Assay forms in which such an antibody can be applied include, but are not limited to, ELISA, microarray, RIA, FACS, Western blotting, chromatography, and histochemistry.

In embodiment of the present invention the biological sample measured, is a biological body fluid, such as, but not limited to blood, serum, synovial fluid or urine samples. The biological fluid may be used as it is, or it may be purified prior to the contacting step. This purification step may be accomplished using a number of standard procedures, including but not limited to, cartridge adsorption and elution, molecular sieve chromatography, dialysis, ion exchange, aluminia chromatograpy, hydroxyapatite chroma-tography, and combinations thereof.

In a further embodiment, the invention provides a method for detecting the amount of HRGYPGLDG (SEQ ID NO:1) epitope containing collagen type II derived fragments in urine or serum. A urine sample is contacted with an antibody specific towards an epitope within the amino acid sequence HRGYPGLDG (SEQ ID NO:1), essentially all collagen type II fragments in urine containing this epitope will be bound by such an antibody. The amount of fragments bound by the antibody will be detected by methods well known in the art.

Typically, the epitope bound by antibodies reactive with HRGYPGLDG (SEQ ID NO:1) may comprise five or more amino acids, e.g. the first five amino acids of the sequence.

In a preferred embodiment for measuring cartilage degradation the antibody utilized for detection only recognizes the unwound form of collagen type II or fragments thereof and not the wound form. It will be possible, in tissue or synovial fluid samples for example, to access a ratio between unwound and wound collagen type II or fragments thereof, this can be related to the collagenase activity in the joint from which the sample has been retrieved. Denatured helical collagen domains might be retained in the tissue by cross-linking and fibrillar packaging. This may complicate detection according to the present invention in cartilage tissue samples. To address this problem, the biological sample may first be contacted with an enzyme having the ability to selectively cleave unwound collagens without cleaving the HRGYPGLDG (SEQ ID NO:1) epitope. Such enzymes could be, but is not limited to, trypsin or chymotrypsin, which are unable to cleave wound collagen. The fragments of unwound collagen are then extracted from the biological sample to produce an extract of unwound collagen fragments. This extract can then be assayed as mentioned in the above.

The method of the present invention is preferably used to detect or monitor catabolic processes in joint tissue, growth plates or intervertebral disks. Disorders associated with such catabolic processes of the cartilage tissue are for example, various forms of arthritis, such as rheumatoid arthritis (RA), psoriasis arthritis, osteoarthritis (OA), yersinia arthritis, pyrophosphate arthritis, gout (arthritis urica), septic arthritis or vertebral disk related disorders such as, but not limited to, degenerative disc disease or ankylosing spondylitis. Disorders of the growth plate are Kashin-Bech, acromegali and dwarfism.

Antibodies with properties as previously described, are raised against a synthetic peptide constituting the HRGYPGLDG (SEQ ID NO:1) sequence or another suitable protein or peptide fragment containing this sequence or at least an epitopic sequence thereof. Such an antibody possess reactivity toward collagen type II protein or fragments thereof from any species containing this epitope, among these are cow, dog, mouse, human, horse and rat. The peptide is used as an antigen for immunization. The peptide is emulsified in an adjuvant medium, preferably incomplete Freund's adjuvant and injected subcutaneously or into the peritoneal cavity of a mammalian host, preferably a rodent most preferred rabbits, even more preferred mice. To enhance immunogenic properties of the antigenic peptide, it can be coupled to a carrier protein before emulsified in an adjuvant medium. Useful carriers are proteins such as keyhole limpet hemocyanin (KLH), edestin, albumins, such as bovine or human serum albumin (BSA or HSA), tetanus toxoid, and cholera toxoid, polyaminoacids, such as poly-(D-lysine-D-glutamic acid). Booster injections may be given at regular intervals until an immune response is obtained, the last injection may be given intravenously to ensure maximal B-cell stimulation.

Antisera will be screened for their ability to bind an epitope within the HRGYPGLDG (SEQ ID NO:1) sequence. Their specificity between unwound and wound collagen type II or fragments thereof, as well cross reactivity with other collagens will be assessed. Antisera from the most promising hosts may be used in their crude form or purified.

Monoclonal antibodies may be generated from immunized mice with the most promising antibody titre, by fusing lymphocytes isolated from the spleen of these mice with a myeloma cell line. The generated hybridoma clones are screened for antibodies with reactivity toward an epitope within the HRGYPGLDG (SEQ ID NO:1) sequence, and cell lines can be established for production and purification of monoclonal antibodies.

Methods for polyclonal and monoclonal antibody production and screening are well known in the art and other methods than the described can also be utilized.

One embodiment of the present invention constitutes the development of a diagnostic kit for use in detection and/or monitoring of cartilage degradation. This includes an antibody recognizing an epitope comprised in the following sequence HRGYPGLDG (SEQ ID NO:1), located in type II collagen or fragments thereof, preferably the antibody recognizes unwound collagen type II and not the wound form. Most preferred are antibodies of the present invention, either alone or with a second antibody with specificity towards the first antibody or another part of the epitope containing fragment. The kit can be applied on mammalian body fluids or extracts of cells or tissues, preferably derived from humans. For competition detections a peptide between 6 and 20 amino acids, in which a succession of amino acids is equivalent to the binding epitope for one of said antibodies, might be supplied either in a labeled or non labeled form. The antibodies may be labeled by joining them, either covalently or non-covalently, with a reporter molecule. Suitable reporter molecules or labels, which may be used for ease of detection, include radionuclides, enzymes, fluorescent, chemilumi-nescent, or chromogenic agents as well as substrates, cofactors, inhibitors, magnetic particles, and the like. One of the non-labeled antibodies or a peptide of the kit might be immobilized, preferably on a solid surface like a micro-titter plate, possibly by conjugation to a suitable protein carrier like BSA.

Figure 1:
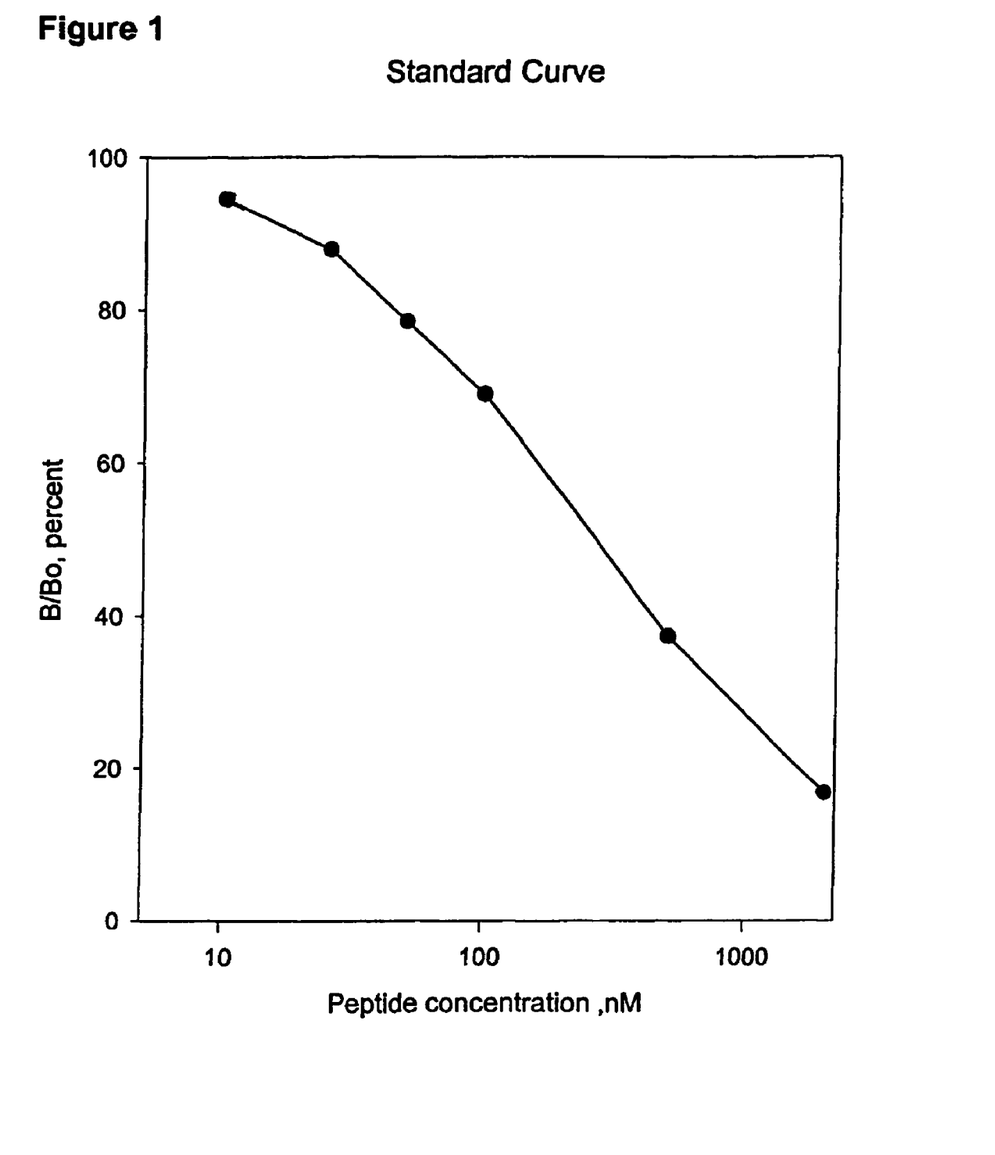
FIG. 1 shows a standard curve for collagen type II immunoassay in a semi-logarithmic plot.
Figure 2:
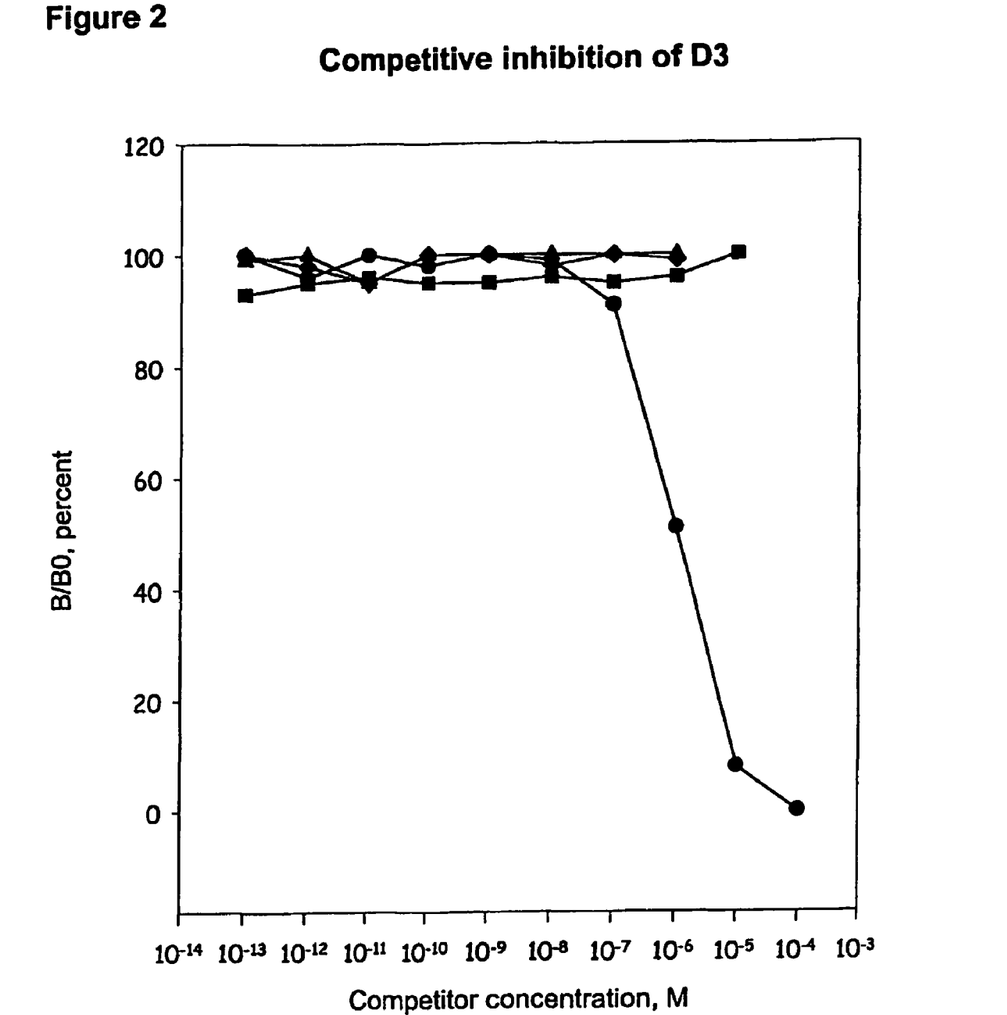
FIG. 2 graphically illustrates competitive binding inhibition of D3.
Figure 3:
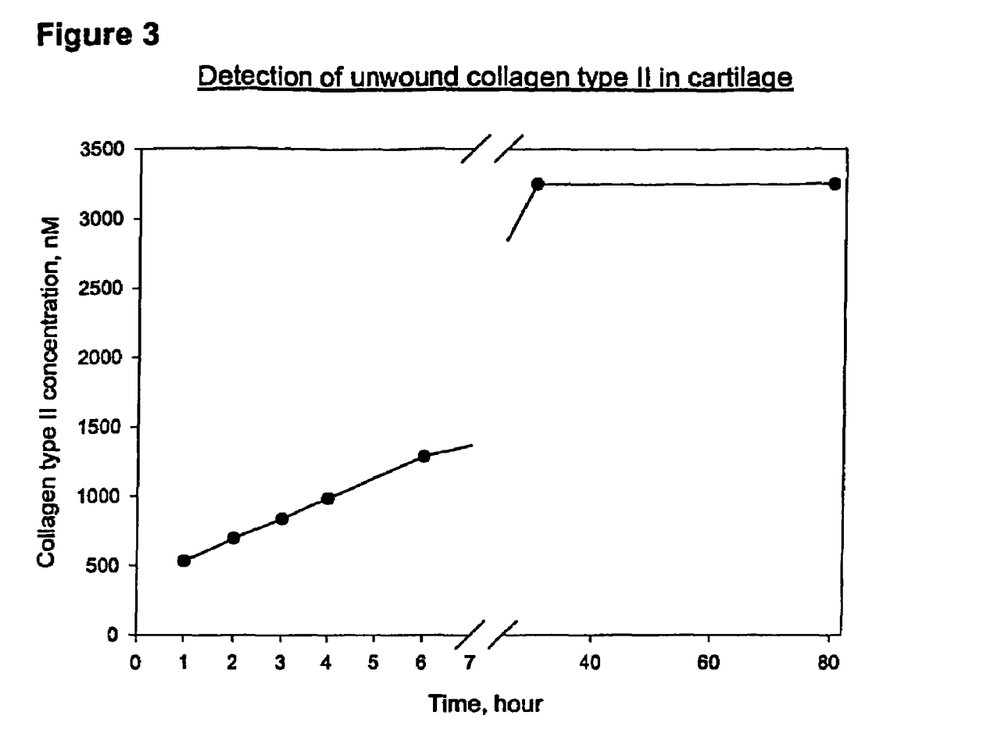
FIG. 3 graphically illustrates detection of unwound collagen type II within cartilage.
Figure 4:
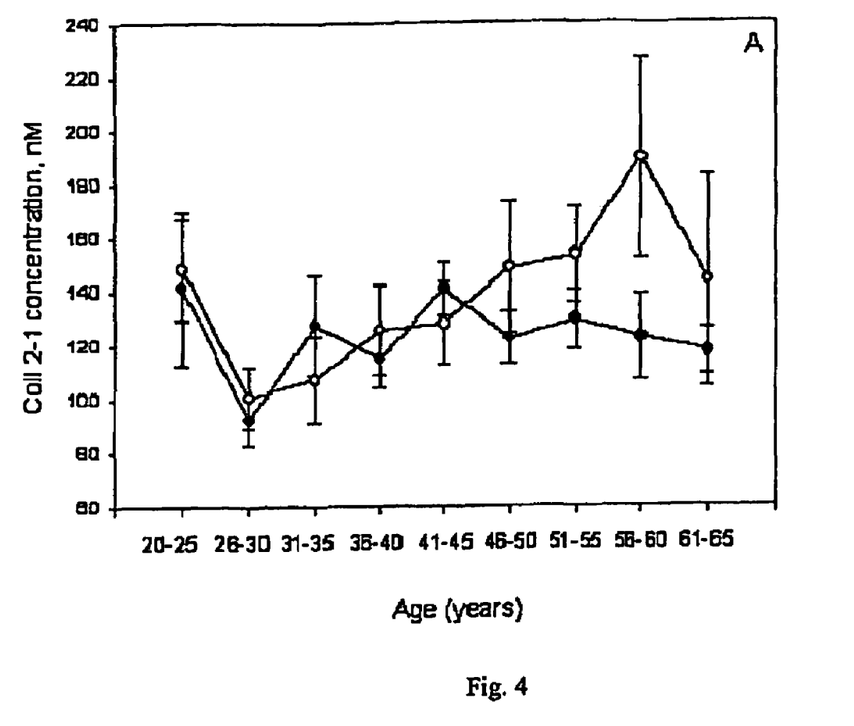
FIG. 4 graphically illustrates results from Example 5.
Figure 5:
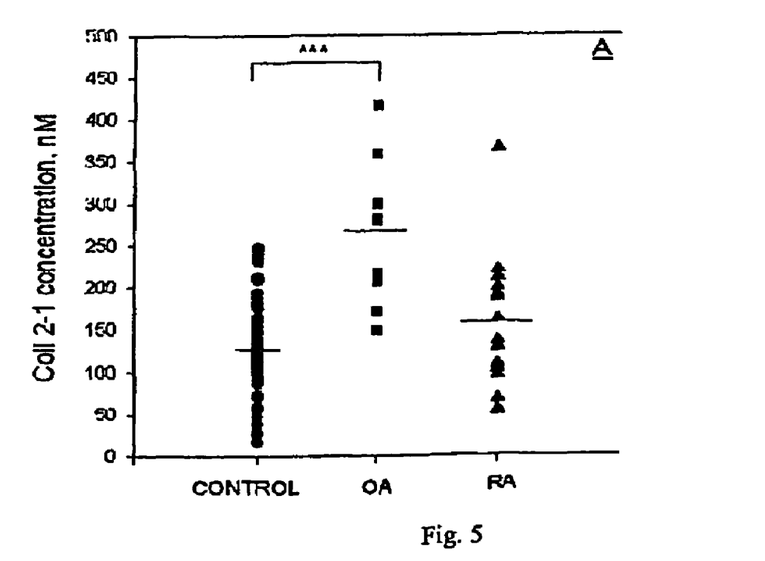
FIG. 5 graphically illustrates results from Example 6.
Figure 6:
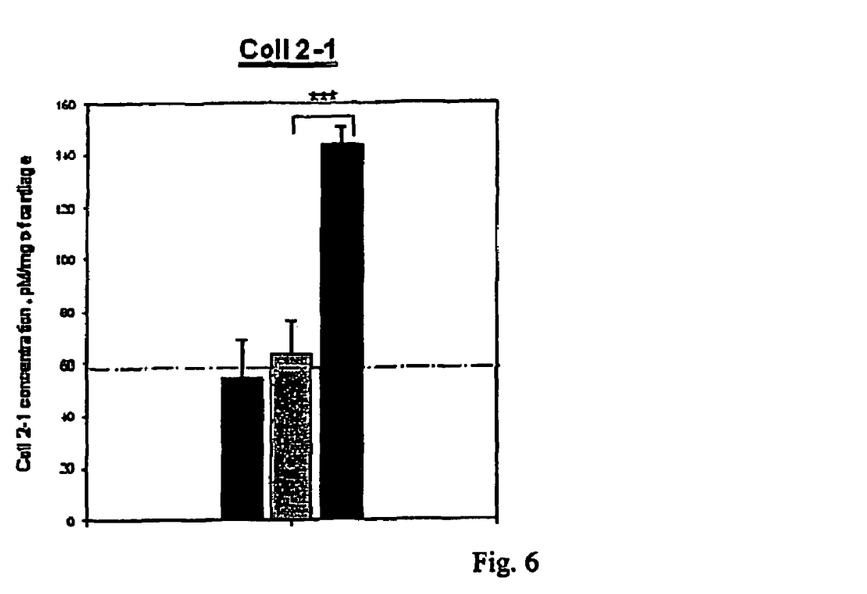
FIG. 6 graphically illustrates results from Example 7.
Figure 7:
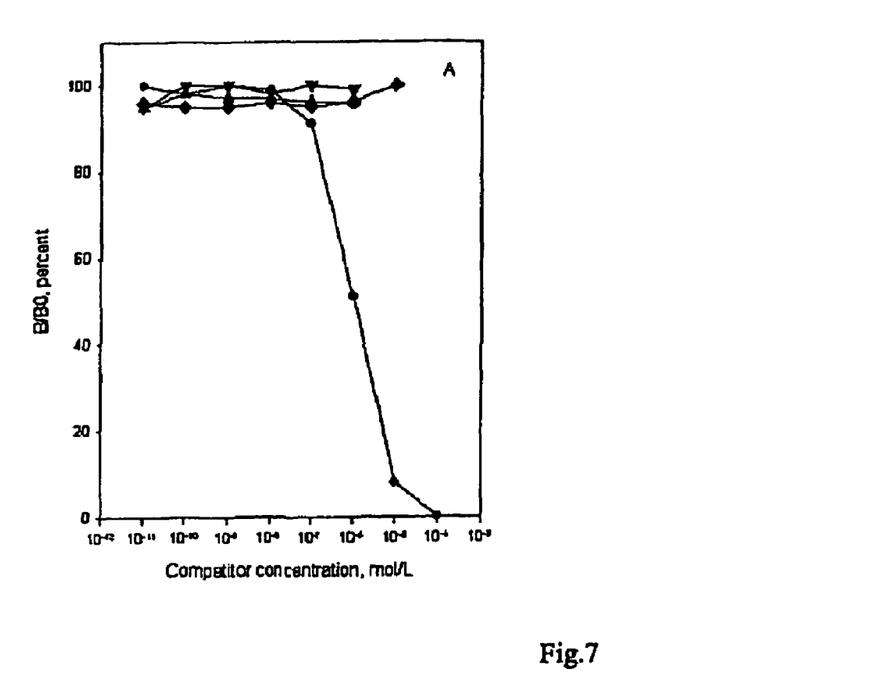
FIG. 7 graphically illustrates results from Example 8.

The invention will be further described and illustrated with reference to the accompanying drawings, in which:

FIG. 1 shows a standard curve for collagen type II immunoassay in a semi-logarithmic plot. The concentration of free antigen is in nM. B/Bo represents the ratio between antibody bound to coated antigen in the presence of free antigen (B) or in the absence of free antigen (Bo) and is given in percentage;

FIG. 2 shows competitive inhibition of antiserum coll2-1 D3 binding to HRGYPGLDG (SEQ ID NO:1) coated plates using HRGYPGLDG (SEQ ID NO:1) (●), native type II collagen (■), type I collagen ( ) and BSA (♦) as competitors. B/Bo represents the ratio between antibody bound to coated antigen in the presence of competitor antigen (B) or in the absence of competitor antigen (Bo) and is given in percentage;

FIG. 3 shows antiserum Coll 2-1 D3's ability to bind collagen type II within cartilage (3 g/10 ml) in relation to the duration of collagenase A (0.5 mg/ml) treatment;

FIG. 4 shows results from Example 5 and illustrates the physiological variation of Coll2-1 levels in urine according to age range and sex. (men black dots, women white dots);

FIG. 5 shows results obtained in Example 6 and demonstrates that OA patients have more elevated Coll2-1 levels than RA patients and control individuals;

FIG. 6 shows results obtained in Example 7 demonstrating that human articular cartilage explants produce Coll2-1 in vitro; and FIG. 7 shows results obtained in Example 8 providing a cross reactivity determination of antibody anti-coll2-1.

EXAMPLES

Example 1

Collagen Type II Immunoassay

Antisera:

A sequence of nine amino acids (His-Arg-Gly-Tyr-Pro-Gly-Leu-Asp-Gly) derived from the triple helical region of type II collagen [(α1)II] was synthesized using standard Fmoc solid-phase peptide synthesis (HBTU/HOBt protocol) (Chan & White, 2000).

The amino acid sequence was conjugated to thyroglobulin by a carbodiimide procedure (Soinila et al 1992).

Rabbits were injected intraperitoneally with 1 ml of the conjugate emulsified in complete Freund's adjuvant. The conjugate and the adjuvant were mixed in equal volumes. Injections were repeated four times every month with a similar amount of conjugate in incomplete Freund's adjuvant. Ten days after the last injection, the rabbits were sacrificed for the final bleeding. Blood was collected and centrifuged for 10 minutes at 1500×g at 4° C. The supernatants were stored at −20° C.

Five antisera, identified as Coll2-1 D1, D2, D3, D4 and D5, was obtained and their specificity were tested with the competitive inhibitors HRGYPGLDG (SEQ ID NO:1), native type II collagen, type I collagen and BSA.

Competitive ELISA:

A competitive immunoassay was developed to quantify breakdown products of type II collagen containing following sequence HRGYPGLDG (SEQ ID NO:1). Synthetic HRGYPGLDG (SEQ ID NO:1) peptides were conjugated to BSA by BS³ [Bis(sulfosuccininimidyl) suberate, Pierce, Rockford, USA]. The conjugated peptides were coated to microtiter plates (NUNC, Denmark) at 50 ng/ml in 0.08 M NaHCO$_3$ pH 9.6 for at least 48 hours at 40° C. The coated microtiter plates were saturated with 400 μl/wells of saturation buffer (KH$_2$PO$_4$ 1.5 mM, Na$_2$HPO$_4$ 8 mM, KCl 2 mM, NaCl 138 mM, BSA 0.5%, lactose monohydrate 5.3% ph 7.2) for 90 minutes at room temperature. Fifty μl of either calibrators (to generate a standard curve), controls or unknown samples, diluted in Ultroser G (Gibco) were pipetted into appropriate wells in the microtiter plate, followed by 100 μl antiserum (see above) diluted 1/40000. Samples were mixed by rotating the plate and incubated 1 hour at room temperature. After three successive washings with washing buffer (Tris 25 mM, NaCl 50 mM pH 7.3), 100 μl of horseradish peroxidase-conjugated goat antibodies to rabbit IgG (Biosource, Belgium) were added to each well and incubated 1 hour at room temperature. After another washing step, 100 μl of freshly prepared enzyme substrate (TMB, Biosource, Belgium) were added to each well. After 15 minutes incubation, the reaction was stopped with 100 μl 4M H$_3$PO$_4$. The absorbance was read with a microplate reader (Labsystem iEMS Reader MF, Finland) at 450 nm and corrected for absorbance at 620 nm. A standard curve was constructed on a log-linear graph by plotting the B/Bo of 6 calibrators (2000 to 10 nM) (FIG. 1). The concentration of HRGYPGLDG (SEQ ID NO:1) containing peptides in the unknown samples and controls, were determined by interpolation on the calibration curve.

Example 2

Characterization of Antisera Coll2-1 D1-5

Specificity

The antisera produced, were tested for their specificity for HRGYPGLDG (SEQ ID NO:1), by use of the immunoassay described in example 1. To test for specificity HRGYPGLDG (SEQ ID NO:1) peptide, collagen type II, collagen type I or BSA, was added in increasing concentrations.

Native type II collagen, type I collagen and BSA, was not able to compete with the coated HRGYPGLDG (SEQ ID NO:1) peptide in the applied concentrations, shown for Coll2-1 D3 in FIG. 2.

The following experiments are carried out utilizing antiserum Coll2-1 D3.

Detection Limit

The detection limit of the assay described in example 1, is calculated as the mean (M) Bo value of 21 determinations of standard A minus 3 times the standard derivation (SD) of Bo ($M_A - 3 \ast SD_A$). For Coll2-1 D3 the detection limit was 17 nM.

Coefficients of Variation

Serum from three patients with OA, which were candidates for hip or knee prosthesis, was assayed for HRGYPGLDG (SEQ ID NO:1) containing collagen type II or fragments thereof. The assays were repeated 10 times to assess the intra-assay coefficient of variation. The CV calculations were performed as follows (SD/Mean concentration)*100%.

| | INTRAASSAY | |
|---|---|---|
| | Concentration (nM) | CV (%) |
| Patient 1 | 109.86 ± 9.1 | 8.3 |
| Patient 2 | 95.07 ± 7.2 | 7.6 |
| Patient 3 | 173.48 ± 15.2 | 8.7 |

Dilution Test

Human serum samples were diluted to ensure that their dilution curves were parallel to the standard curve.

| Serum Dilution | Measured concentration (nM) | Expected concentration (nM) | Recovery (%) |
|---|---|---|---|
| Undiluted | — | 1200 | |
| ½ | 597.30 | 600 | 99.5 |
| ¼ | 282.80 | 300 | 94.3 |
| ⅛ | 139.95 | 150 | 93.3 |
| 1/16 | 81.98 | 75 | 109.3 |

Analytical Recovery

A serum sample was spiked with known concentrations of synthetic HRGYPGLDG (SEQ ID NO:1) peptide, to ensure that its presence would not effect the recovery of collagen type II or fragments thereof present in the serum sample.

| Added peptide concentration (nM) | Measured concentration (nM) | Expected concentration (nM) | Recovery (%) |
|---|---|---|---|
| 0.00 | 81.00 | — | — |
| 44.98 | 132.14 | 125.98 | 104.9 |
| 56.69 | 136.46 | 137.69 | 99.1 |
| 110.82 | 168.87 | 191.82 | 88.0 |
| 212.33 | 265.35 | 293.33 | 90.5 |
| 276.34 | 306.12 | 357.34 | 85.7 |
| 653.20 | 720.68 | 734.2 | 98.2 |
| 1297.25 | 1406.75 | 1378.25 | 102.1 |

Example 3

Antiserum Coll2-1 D3 Recognizes Unwound but not Wound Type II Collagen

As already shown in the specificity assay of example 2, Coll2-1 D3 does not bind native (wound) collagen type II, as this is not able to compete with the antiserum binding to coated HRGYPGLDG (SEQ ID NO:1) peptide. In the following example digestion of cartilage with collagenase A from *Clostridium histolyticum*, was used to asses the ability of Coll2-1 D3 to bind unwound collagen type II compared to wound collagen type II (FIG. 3).

Collagenase Digestion

Cartilage obtained from surgery of healthy individuals is cultured in petri dishes at 3g/10 ml medium (DMEM GIBCO serum free) at 37° C. and 5% CO$_2$. Cartilage degradation is initiated at time 0 by addition of 0.5 mg/ml collagenase A from *Clostridium histolyticum*. At times 1, 2, 3, 4, 6, 30 and 80 h, 100 μl medium is removed, centrifuged at 5000×g and subjected to the immunoassay described in example 1.

It is seen in FIG. 3 that the collagen becomes detectable in the assay with lapse of time, indicating that the unwound form but not the wound form is reactive with the antibody.

Example 4

Detection of Collagen Type II Degradation in Patients with OA, which were Candidates for Hip or Knee Prosthesis Versus Young Healthy Individuals Sera from healthy volunteers and patients were collected and subjected to the assay described in example 1, utilizing antiserum Coll2-1 D3. The concentration in nM of HRGYPGLDG (SEQ ID NO:1) containing collagen type II or fragments thereof looked as follows:

| Healthy (n = 30) | OA patents (n = 4) |
|---|---|
| 107.56 ± 77.00 | 144.46 ± 109.23 |

Example 5

Physiological Levels of Coll 2-1 in Healthy Men and Women

To establish reference values for Coll 2-1, sera were collected from 242 healthy ambulatory subjects attending a blood donor centre in Liege, Belgium. None of the study subjects had any evidence of arthritis or other inflammatory disease. None was currently taking any medication known to modify arthritic disease or influence joint metabolism. This group was composed of 170 men and 72 women, aged from 20 to 65 years (mean: 42.8±1.4 years). The mean age of women was 42.7±1.0 years old and the mean age of men was 42.8±1.4 years old.

When the population was stratified by age in 5 years brackets, Coll 2-1 serum levels were lower in younger individuals than older (FIG. 4). The comparison of peptide levels by sex showed that after 45 years of age, Coll 2-1 concentration was higher in women than in men but the difference did not reach statistical significance. However, when subjects aged from 46 to 55 years corresponding to the early postmenopausal women were removed, Coll 2-1 levels were higher in pre-menopausal women than in post-menopausal women.

Coll2-1 fragment level drops for both sexes between age 20-26 and then rises again gradually from age 26 to after menopause for the female group whereas the males showed a more stable level of Coll2-1 along their life span (FIG. 4).

Example 6

OA Patients have more Elevated Coll2-1 Levels than RA Patients or than Normal Individuals An important clinical issue is whether levels of the Col2-1 marker are elevated in arthritis. To study this, serum samples were obtained from a cross-sectional panel of arthritis patients comprising 10 OA patients (4 women and 6 men aged over 45 years) who were candidates for arthroscopy. Arthroscopy was performed for diagnosis and/or shaving of the meniscus and cartilage lesions. Sera were collected 24 hours prior to surgery. These subjects had no radiological signs of OA but all had cartilage lesions identified by arthroscopy. All subjects had a normal leukocytosis and a C-reactive protein (CRP) level inferior to 5 mg/L. Furthermore, these patients did not take any nonsteroidal anti-inflammatory drugs during the year before the intervention.

Coll 2-1 concentration was also measured in serum samples of 14 patients with early RA. At the sampling time, these patients had not received any medication, and all had a C-reactive protein level above 5 mg/L.

A control group representing normal individuals showed a lower level of Coll2-1 fragment compared with RA patients and OA patients (FIG. Y+1). Coll2-1 levels were highest in OA patients compared to RA patients or controls. These results allow with this assay to distinguish between normal individuals, OA patients and RA patients as shown in FIG. 5.

Example 7

Human Articular Cartilage Explants Produce Coll2-1 in Vitro

Articular cartilage explants allow also the study of Coll2-1 release in the conditioned medium and by that the progression of cartilage degradation according to environmental factors such as cytokines concentration for example. Articular cartilage was obtained from adult human patients undergoing joint replacement surgery and the cartilage was excised either as cylindrical plugs (5-30 mg) or as slices (20-30 mg). The explants were cultured in 96-well plates in 200 mL serum free DMEM medium, (FIG. 6, left hand bar) or in the presence of recombinant human IL-1α5 ng/mL (Sigma, St. Louis, USA), Oncostatin M 50 ng/mL (Sigma, St. Louis, USA) and human plasminogen 10 µg/mL (Sigma, St. Louis, USA) (FIG. 6, middle bar). Plasminogen is a physiological MMP activator that induces collagen type II degradation. Furthermore the MMP activator APMA (aminophenyl mercuric acetate, SIGMA, St Louis, USA) was added with the results indicated in FIG. 6 right hand bar. The conditioned medium was harvested at various time points for measurement of Coll2-1 This example shows how the cytokines IL1 and oncostatin (OSM) influence the release of Coll2-1 in the conditioned medium from cartilage explants. Addition of the catabolic cytokines IL1 and oncostatin (OSM) influence the release of Coll2-1 in the conditioned medium from cartilage explants. Alone IL1, oncostatin and plasminogen had no influence on cartilage degradation. However a significant level of Coll2-1 could be detected in conditioned medium of cartilage explants when the plasminogen activator APMA was also added to the medium. This relates the Col2-1 marker directly to catabolic processes of articular cartilage and demonstrates that the marker is released in conjunction with collagenolytic activity.

Example 8

Development of an Assay Specific for a Collagen Type II Epitope Derived from the α-Helical Region (Coll2-1 ELISA)

Reagents and Buffers for Immunoassays

The coating buffer was 0.08 M $NaHCO_3$ pH 9.6. The saturation buffer was composed of 1.5 mM $KH_2PO_4$, 8 mM $Na_2HPO_4$, 2 mM KCl, 138 mM NaCl, 5 g/L bovine serum albumin (BSA), 53 g/L lactose monohydrate pH 7.2. The washing buffer was a solution of 25 mM Tris, 50 mM NaCl pH 7.3. The standard curve and the dilution of samples, when it was necessary, were realized in 10 mM phosphate buffer saline, 138 mM NaCl, 7 g/L BSA, 1 ml/L Tween 20 pH 7.0. The dilutions of the antisera and of the second antibody were done in 10 mM phosphate buffer saline, 138 mM NaCl, 2 g/L BSA, 1 ml/L Tween 20 pH 7.0.

Immunization

Rabbits were injected intra-peritoneally with 1 ml of the conjugated peptides (0.5 mg/ml) emulsified in complete Freund's adjuvant. The conjugate and the adjuvant were mixed in equal volumes. Injections were repeated four times every month using the same peptide concentration that those of the first injection in incomplete Freund's adjuvant. Ten days after the last injection, the rabbits were sacrificed. Blood was collected and centrifuged for 10 min at 2500 rpm at 4° C. The supernatant was kept and stored at −20° C. At each bleeding, antisera were screened by titration experiment for the presence of anti-HRGYPGLDG (SEQ ID NO:1) antibody. The antisera with the highest titers were selected for the following experiments.

Antiserum Specificity

The specificity of the two selected antisera (D3) was investigated by competitive inhibitions procedure. Coll 2-1, Coll 2-1 $NO_2$, native type II collagen, nitrated type II collagen, heat denatured type II collagen (obtained by heating a solution of native human type II collagen at 100° C. for 30 min), native type I collagen, nitrated type I collagen, BSA, nitrated BSA and L-3-nitro-tyrosine residue were used as competitors. Briefly, immunoplates were coated overnight at 4° C. with 100 µl of the antigen (Coll 2-1) conjugated to BSA by $BS^3$ (40 ng/100 µl). After washing, the plates were blocked with 400 µl of saturation buffer at room temperature. Fifty µl of buffer with or without the different competitors at increasing concentrations (from $10^{-4}$ to $10^{-11}$ mol/L) and 100 µl of antiserum diluted to obtain 1.5 of D.O. were incubated 1 h at room temperature. Microplates were then washed, 100 µl of a goat antibody conjugated to horseradish peroxidase (Biosource, Belgium), diluted at 1/5,000, was added and incubated 1 h at room temperature. After washing, 100 µl of freshly prepared enzyme substrate (TMB, Biosource, Belgium) was added into each well. The reaction was stopped with 100 µl of $H_3PO_4$ 4M. The coloration was read at 450 nm, corrected for absorbance at 650 nm.

As seen in FIG. 7, D3 did not recognize native type II collagen, heat denatured type II collagen, type I collagen or BSA. These results suggest that D3 was highly specific for the linear form of Coll2-1. Moreover its non-affinity for native and heated collagen type II also suggests that the recognition of the sequence is highly dependant upon the fact that the fragments of collagen type II are released. The epitope might be hidden in wound collagen, even after heating.

REFERENCES

Billinghurst, R. C., Dahlberg, L., Ionescu, M., Reiner, A., Bourne, R., Rorabeck, C., Mitchell, P., Hambor, J., Diekmann, O., Tschesche, H., Chen, J., Van Wart, H., Poole, A. R., 1997. Enhanced cleavage of type II collagen by collagenases in osteoarthritic articular cartilage. J Clin Invest 99, 1534-1545.

Chan, W. C., White, P. D., 2000 Fmoc solid-phase peptide synthesis: A practical approach, Oxford University Press, Oxford 2000.

Croucher, L. J., Hollander, A. P., 1999. Differential detection of type II collagen N-terminal and C-terminal denaturation epitopes in degrading cartilage. Mol. Pathol 52, 323-331.

Furumitsu, Y., Inaba, M., Yukioka, K., Yukioka, M., Kumeda, Y., Azuma, Y., Ohta, T., Ochi, T., Nishizawa, Y., Morii, H., 2000. Levels of serum and synovial fluid pyridinium crosslinks in patients with rheumatoid arthritis. J Rheumatol 27, 64-70.

Hollander, A. P., Heathfield, T. F., Webber, C., Iwata, Y., Bourne, R., Rorabeck, C., Poole, A. R., 1994. Increased damage to type II collagen in osteoarthritic articular cartilage detected by a new immunoassay. J Clin Invest 93, 1722-1732.

Moller, H. J., 1998. Connective tissue markers of rheumatoid arthritis. Scand J Clin Lab Invest 58, 269-278.

PCT application WO 01/38872, Christgau S., Henriksen D. B., Cloos P., Assay of Isomerized and/or Optically Inverted Proteins and Protein Fragments, Osteometer Biotech A/S (DK), 2001.

Soinila, S., Mpitsos, G. J., Soinila, J., 1992.

Immunohistochemistry of enkephalins: model studies on hapten-carrier conjugates and fixation methods. J Histochem. Cytochem. 40, 231-239.

U.S. Pat. No. 5,641,837, Eyre D. R., Method of detecting collagen degradation in vivo, Washington Research Foundation (Seattle, Wash.), 1997.

U.S. Pat. No. 5,919,634, Eyre D. R., Methods of detecting collagen type II degradation in vivo, Washington Research Foundation (Seattle, Wash.), 1999.

U.S. Pat. No. 6,132,976 Poole A. R., Hollander A. P., Billinghurst R. C., Immunoassay For the Measurement of Collagen Denaturation and Cleavage in Cartilage, Shriners Hospital for Children (Tampa, Fla.), 2000.

U.S. Pat. No. 6,342,361 Qvist P., Bonde M., Method Of assaying Collagen Fragments in Body Fluids, A Test Kit And Means For Carrying Out The Same, Osteometer Biotech A/S (DK), 2002.

Wollheim, F. A., 1996. Predictors of joint damage in rheumatoid arthritis. APMIS 104, 81-93.

The invention claimed is:

1. A kit for performing qualitative or quantitative assay of unwound collagen type II fragments containing amino acid sequence HRGYPGLDG (SEQ ID NO: 1) in a biological sample, the assay comprising contacting the fragments with an antibody that is immunoreactive with an epitope comprised in amino acid sequence HRGYPGLDG (SEQ ID NO: 1) and detecting resulting immunoreaction, and the kit comprising a) the antibody immunoreactive with the epitope comprised in the amino acid sequence HRGYPGLDG (SEQ ID NO: 1) and b) means for detecting immunoreaction between the antibody and the sample.

2. The kit according to claim 1, wherein the antibody bears a detectable label or is immobilized to a solid material.

3. The kit according to claim 1 further comprising a peptide including the epitope and competing with collagen type II or fragments thereof for binding to the antibody.

4. The kit according to claim 3, wherein the peptide bears a detectable label or is immobilized to a solid surface.

* * * * *